(12) United States Patent
Carlsson

(10) Patent No.: US 10,804,971 B2
(45) Date of Patent: Oct. 13, 2020

(54) MEDICAMENT DELIVERY DEVICE

(71) Applicant: SHL MEDICAL AG, Zug (CH)

(72) Inventor: Daniel Carlsson, Enskede (SE)

(73) Assignee: SHL MEDICAL AG, Zug (CH)

(*) Notice: Subject to any disclaimer, the term of this patent is extended or adjusted under 35 U.S.C. 154(b) by 0 days.

(21) Appl. No.: 16/565,794

(22) Filed: Sep. 10, 2019

(65) Prior Publication Data
US 2020/0119769 A1 Apr. 16, 2020

(30) Foreign Application Priority Data
Oct. 15, 2018 (EP) .................................. 18200529

(51) Int. Cl.
H04B 5/00 (2006.01)
A61M 5/50 (2006.01)
H01Q 7/00 (2006.01)

(52) U.S. Cl.
CPC ......... *H04B 5/0062* (2013.01); *A61M 5/5086* (2013.01); *H01Q 7/00* (2013.01); *A61M 2205/14* (2013.01); *A61M 2205/3569* (2013.01); *A61M 2205/60* (2013.01)

(58) Field of Classification Search
CPC ..... H04B 5/0062; A61M 5/5086; A61M 5/14; A61M 5/3569; A61M 5/60; H01Q 7/00
See application file for complete search history.

(56) References Cited

U.S. PATENT DOCUMENTS

2011/0313395 A1* 12/2011 Krulevitch .............. A61M 5/24
604/504
2017/0319787 A1 11/2017 Roedle
2019/0251306 A1* 8/2019 Komaki .................. H01Q 9/26

FOREIGN PATENT DOCUMENTS

| WO | 2010/098931 A1 | 9/2010 |
| WO | 2010/133676 A1 | 11/2010 |
| WO | 2010133676 | * 11/2010 |
| WO | 2018/010931 A1 | 1/2018 |

* cited by examiner

*Primary Examiner* — Yuwen Pan
*Assistant Examiner* — Angelica M Perez
(74) *Attorney, Agent, or Firm* — McDonnell Boehnen Hulbert & Berghoff LLP

(57) ABSTRACT

A medicament delivery device is provided having a proximal part and a distal part, the proximal part being arranged to accommodate a medicament container, an information carrier reader arranged to the distal part, provided with at least one antenna, an information carrier arranged to the proximal part, provided with an antenna, an attachment arrangement for attaching the proximal part to the distal part, which attachment arrangement is designed such that said information carrier may assume at least two different positions when the proximal part is attached to the distal part, wherein said at least one antenna of said information carrier reader is arranged such that it is capable of reading information from said information carrier in any of the different positions that the information carrier may assume.

20 Claims, 5 Drawing Sheets

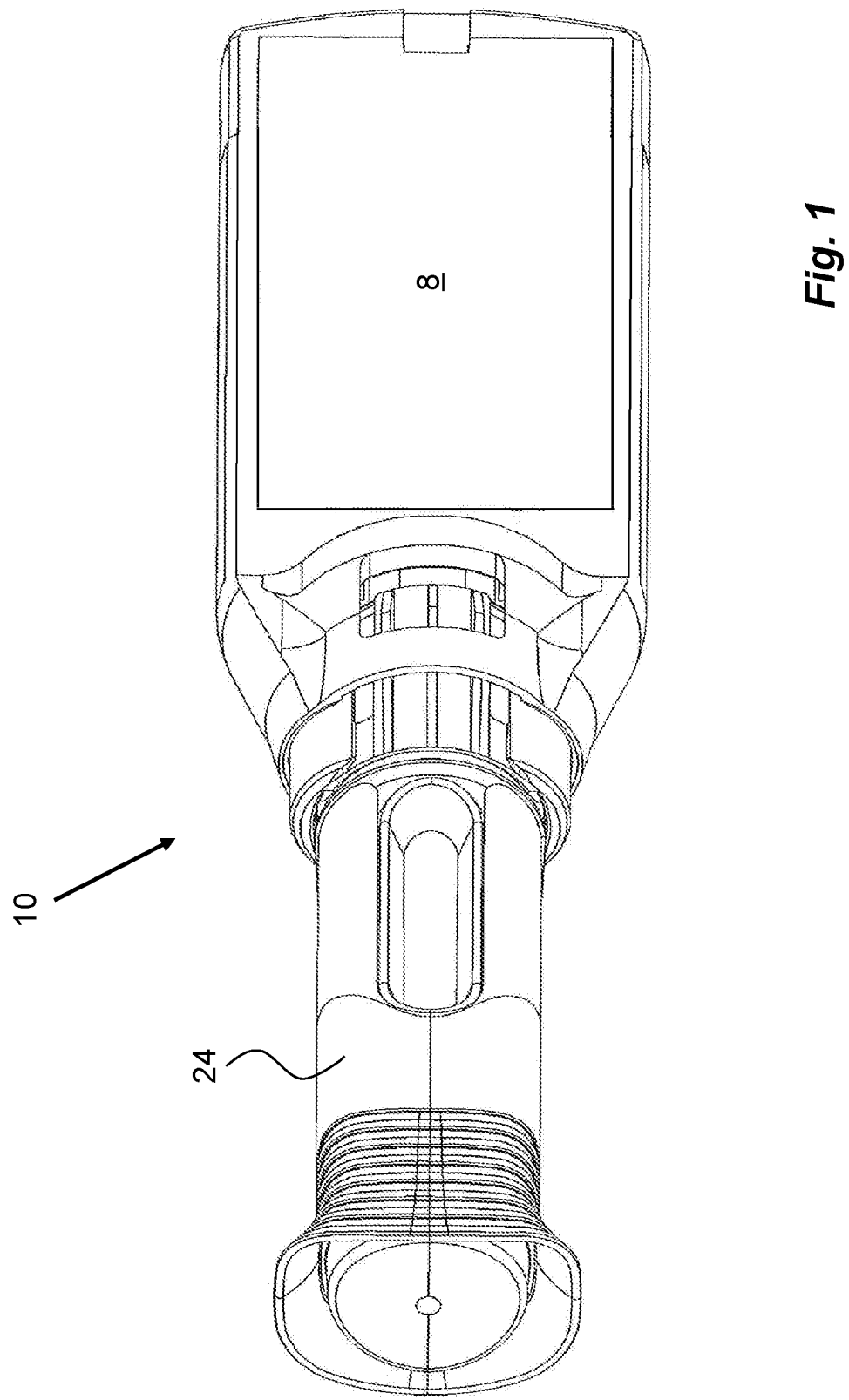

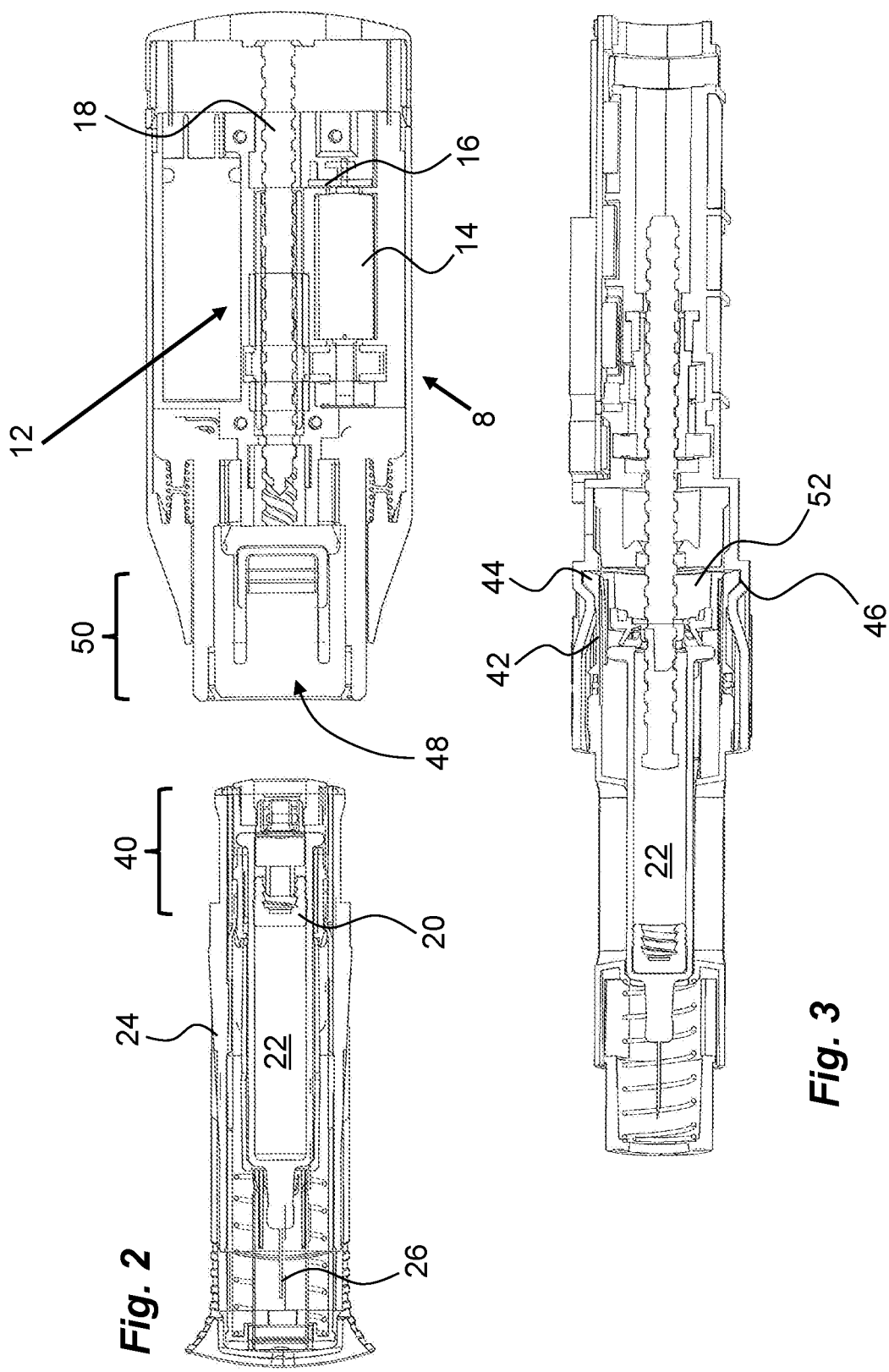

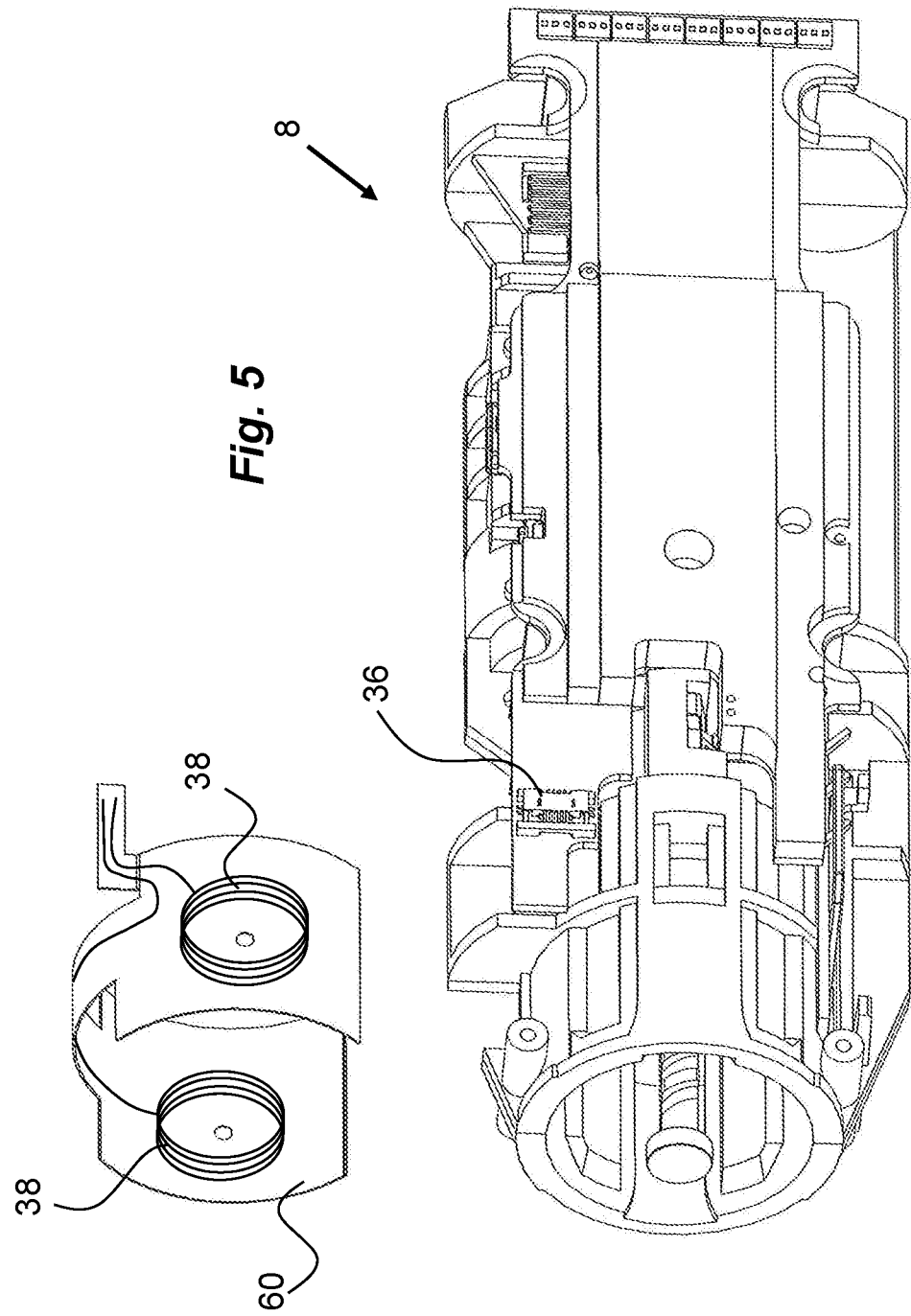

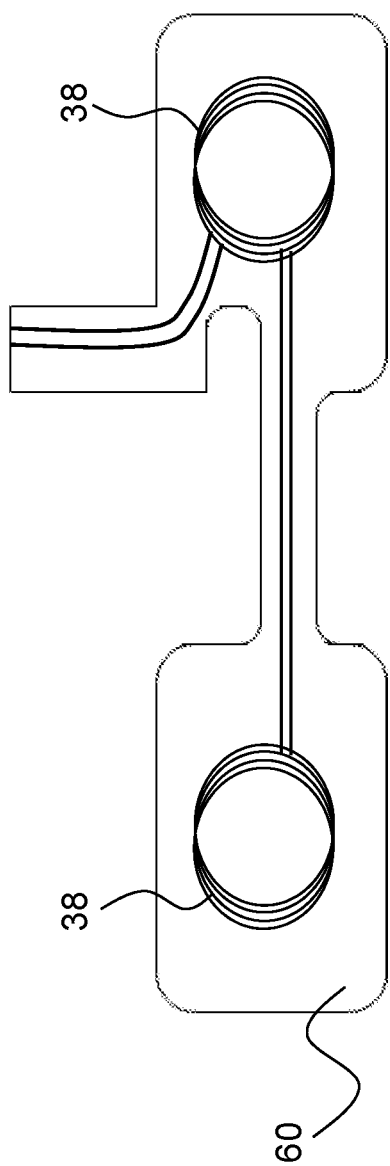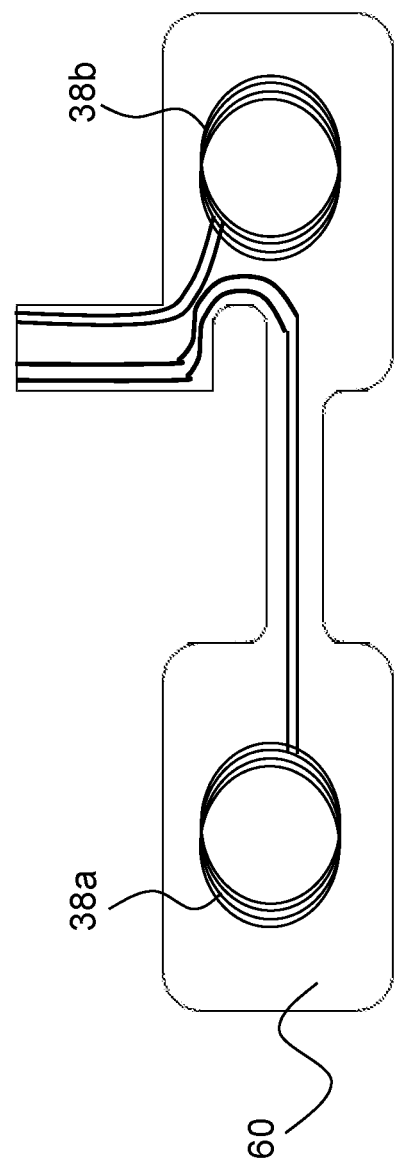

MEDICAMENT DELIVERY DEVICE

CROSS REFERENCE TO RELATED APPLICATIONS

The present application is claims priority to European Patent Application No. 18200529.8 filed Oct. 15, 2018 which is herewith incorporated by reference into the present application.

TECHNICAL AREA

The present disclosure relates to a medicament delivery device provided with arrangements for detecting certain components of the medicament delivery device and in particular components that are removably attached and in particular replaceable and/or disposable.

BACKGROUND

In line with the current trends of developing smart primary containers and the like for medicament delivery devices, so-called rigid needle shields or RNS are used with syringes in particular for self-administration. In this regard, the RNS may be arranged with an information carrier tag such as for instance an RFID-tag. Such solutions are described in the document WO 2018/010931, in which the information carrier tag preferably is fixedly attached to and RNS through co-molding for instance. It is however conceivable that the information carrier tag is attached to the RNS via adhesive labels and the like. The information carrier tag may of course be attached to or integrated in other components of a medicament delivery device. For instance medicament container holders, housing parts, protective caps etc. may be used for combining with an information carrier tag, where the type of component to be attached to depends on what type of information and how different components are handled, shipped, assembled stored etc.

The information carrier tag may be read by external information carrier readers at many different locations and situations throughout the life cycle of medicament delivery devices and/or their components and medicament containers. However, there is also a strong trend to develop medicament delivery devices provided with "smart" functions. These functions may comprise detecting activation of the device, injection sequence and end of injection and may connect these to time stamps, thereby obtaining data regarding for instance adherence to a treatment scheme. The smart functions may then also comprise alerts to a user when a dose is to be administered according to the scheme. All this data obtained can then be transmitted to external sources for data handling. In some cases the smart functions may also comprise information carrier readers in the medicament delivery device that can obtain drug specific data from e.g. medicament containers and/or RNS's attached to these medicament containers. This data can then be used for instance to alert a user that a medicament in the medicament container is about to expire for instance or what type of drug that is contained in the medicament container. Also, if a medicament container is contained in a medicament container holder or a housing part of a medicament delivery device, where these parts may be used once and then replaced, so called disposable parts, an information carrier may be integrated in or attached to these parts and read by an information carrier reader on a main or re-usable part of a medicament delivery device.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

The aim of the present application is to remedy the drawbacks of the state of the art devices. This aim is solved by a medicament delivery device provided with the features of the independent patent claim. Preferable embodiments of the disclosure form the subject of the dependent patent claims.

According to a main aspect of the application, it comprises a medicament delivery device may comprise a proximal part and a distal part, the proximal part being arranged to accommodate a medicament container. The medicament delivery device may further comprise an information carrier reader arranged to the distal part, provided with at least one antenna and an information carrier arranged to the proximal part, provided with an antenna.

An attachment arrangement is arranged for attaching the proximal part to the distal part, which attachment arrangement is designed such that the information carrier may assume at least two different positions when the proximal part is attached to the distal part, wherein the at least one antenna of the information carrier reader is arranged such that it is capable of reading information from the information carrier in any of the different positions that the information carrier may assume.

The solution will provide the possibility of obtaining information from the information carrier in any attachment position. The user does not have to check and/or align the parts so that it is ascertained that the information carrier will be in a position in relation to the distal part so that information may be obtained. Further, the attachment arrangement does not have to be adapted to allow only one attachment position.

According to one aspect, the proximal part may have an extension along a longitudinal axis wherein the at least two positions comprise different rotational positions around the longitudinal axis. In this respect, a distal end of the proximal parts forms a first engagement area that is designed to fit into and engage with a second engagement area of a cavity of the distal part, wherein the attachment arrangement is provided between the first and the second engagement areas.

Further, the antenna of the information carrier may be arranged in the first engagement area of the proximal part and the at least one antenna of the information carrier reader may be arranged and extending in the second engagement area so as to enable reading of the information carrier in any of the rotational position that the information carrier may assume.

Preferably the first and the second engagement areas have generally cylindrical shapes, wherein the at least one antenna of the information carrier reader is extending around a substantial part of the circumference of the second engagement area.

According to one aspect, the at least one antenna of the information carrier reader may be a single antenna. As an alternative, the at least one antenna of the information carrier reader may comprise several antennas. In the latter case, different antennas may be arranged to cover different positions that the information carrier may assume. In this regard, the information carrier reader may be programmed such that only one antenna is active at the time so as not to interfere in the reading of the information carrier.

Either the proximal part is disposable after use or the proximal part is reusable and the medicament container is disposed after use.

These and other aspects of, and advantages with, the present disclosure will become apparent from the following detailed description of the disclosure and from the accompanying drawings.

BRIEF DESCRIPTION OF THE FIGURES

In the following detailed description of the disclosure, reference will be made to the accompanying drawings, of which FIG. 1 shows one example of a medicament delivery device according to the present application, FIG. 2 shows a longitudinal cross-section of the medicament delivery device of FIG. 1 with a proximal part and a distal part separated, FIG. 3 shows a longitudinal cross-section taken 90 degrees in relation to the cross-section of FIG. 2 and with the proximal part and the distal part attached to each other, FIG. 5 is a perspective view of the distal part of the medicament delivery device with the antenna assembled as well as the proximal part with its information carrier and antenna, FIG. 6 shows the antenna of FIG. 4 with a different layout, and FIG. 7 shows the antenna of FIG. 4 with yet another layout.

DETAILED DESCRIPTION

Figure 4:
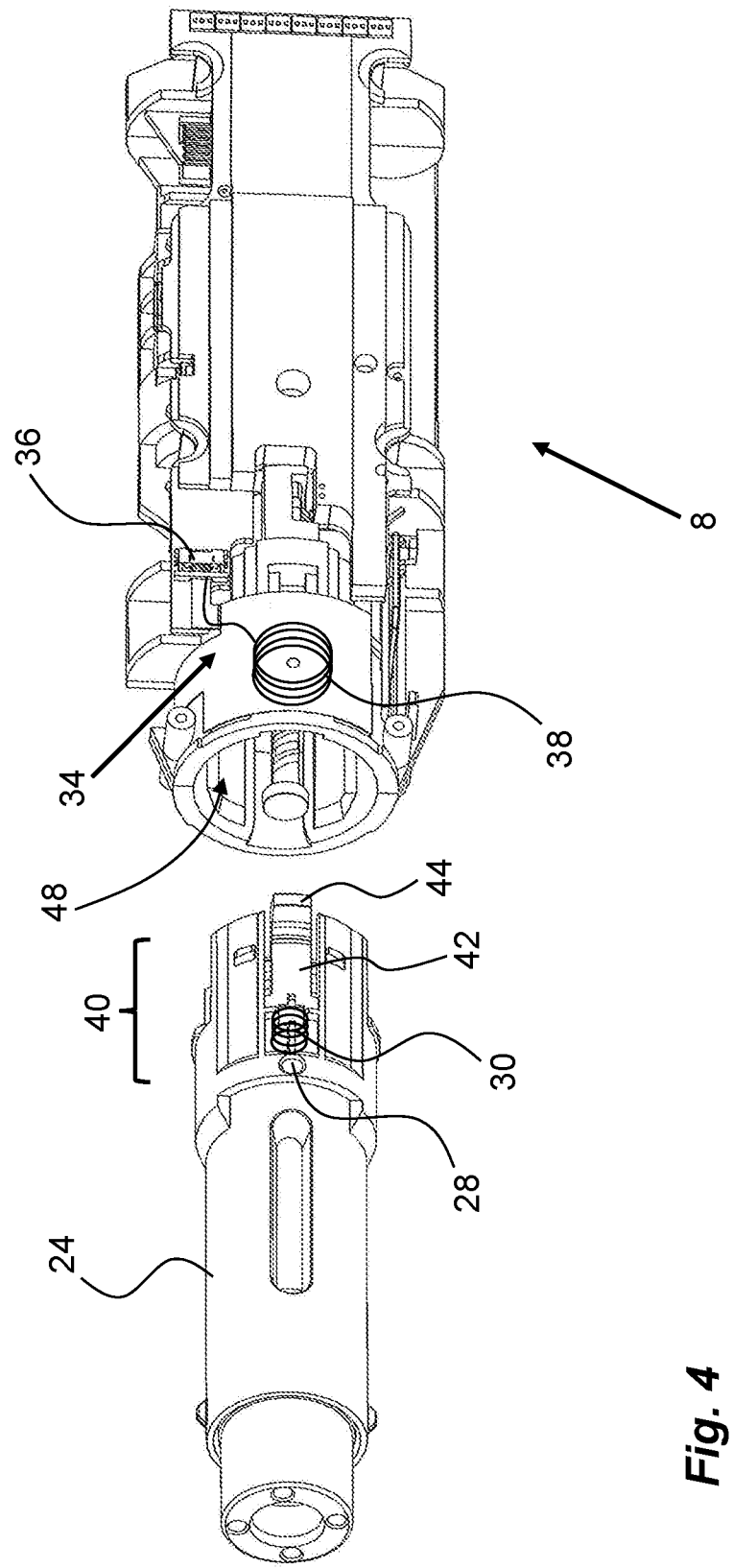
FIG. 4 is a perspective view of the distal part of the medicament delivery device of FIG. 1, with an outer housing removed and with an antenna of an information carrier reader detached.

The present application may be implemented in a medicament delivery device 10 as shown in FIGS. 1 and 2. In this instance the medicament delivery device 10 is of the type with a main or distal part 8 having an electric drive unit 12 with an electric motor 14, FIG. 2, that via appropriate transmission 16 can drive a plunger rod 18 in a proximal direction for acting on a stopper 20 of a medicament container 22 that is placed in a proximal part 24 of the medicament delivery device 10. The movement of the stopper 20 will cause a dose of medicament to be delivered to a dose delivery site through a medicament delivery member such as an injection needle 26.

This type of medicament delivery device 10 is rather expensive to manufacture and is intended to be used many times, a so called re-usable medicament delivery device 10. This means that the medicament container 22 has to be replaced after a dose delivery sequence. There could be several different scenarios. Either the medicament container 22 is a syringe which has an injection needle 26 fixedly attached as seen in FIG. 2, in which case the medicament container 22 has to be replaced after each injection. On the other hand, the medicament container 22 could be a so called cartridge on which an injection needle 26 may be releasibly attached. This provides the possibility of the medicament container 22 containing a number of doses and that only the needle is replaced after each dose delivery. The cartridge is then replaced after all doses comprised in one cartridge have been delivered.

In any event, when the medicament container is to be replaced, the medicament delivery device must be arranged to detach a part, usually the proximal part 24, in order to access the medicament container 22. As an alternative, the whole proximal part 24 is removed and replaced with a new proximal part 24 containing a new medicament container 22.

According to the present application, the proximal part 24 of the medicament delivery device is arranged with an information carrier 28, FIG. 4, that comprises data stored therein. Data could be information regarding the medicament, type, batch, manufacturing date, expiry date, etc. The information carrier 28 comprises an antenna 30 that enables reading of stored data from the tag by an information carrier reader. The information carrier may for example be an RFID-tag or NFC-tag. In this regard it is of course possible to use other technologies of near range wireless communication.

The main part or distal part 8 of the medicament delivery device 10 is for this reason arranged with an information carrier reader 34 capable of reading an information carrier 28. The information carrier reader 34 may have an information carrier reader chip 36 provided with data and storage means as well as an antenna 38 for enabling reading of information carriers 28 when the antenna 38 of the information carrier reader 34 and the antenna 30 of the information carrier 28 are within reading distance.

The information carrier 28 could either be moulded into the proximal part 24 of the medicament delivery device 10 during manufacture or it could be included in for example a label that is attached to the proximal part 24. In any event, the information carrier 28 will have a specific position on the proximal part 24.

Since the information carrier reader 34 has a rather short reading range, it is important that the information carrier 28 will be positioned correctly. Further, a distal area of the proximal part 24 has an engagement area 40, hereafter called first engagement area 40 that is arranged with attachment members in the form of oppositely positioned distally directed tongues 42 having outwardly extending protrusions 44. These protrusions 44 are arranged to fit into oppositely positioned recesses 46 on an inner surface of a cavity 48 in the form of a tubular passage in the distal part 8, which inner surface forms a second engagement area 50. After insertion of the proximal part 22, the tongues 42 with the protrusions 44 in the recesses 46 are locked in this position by an appropriate locking element 52, such as a sleeve that is pushed forward so it comes in contact with the inner surfaces of the tongues 42, thereby locking them in the radial direction.

With the design having oppositely positioned attachment members, it is possible to attach the proximal part 24 in two positions rotated 180 degrees in relation to each other. Regarding the reading range of the information carrier reader 34 it is not possible to place the information carrier reader 34 and/or the information carrier 28 so that the information carrier 28 can be read in both positions, it is within range in one position but outside range in the other position.

In order to increase the reading range to cover both positions of the proximal part 24, the information carrier reader 34 is arranged with an antenna arrangement as seen in FIGS. 4 and 5. Here the antenna 38 is arranged on a flexible holder 60, FIG. 5, such that the antenna 38 has been extended to cover 180 degrees of circumference of the second engagement area 50 of the distal part 8. In this way the range of the antenna 38 is extended to cover both positions that the information carrier 28 and its antenna 30 may assume when the proximal part 22 is attached to the distal part 8 with the first engagement area 40 being in engagement with the second engagement area 50 as seen in FIG. 3.

In one embodiment, the antenna 38 is one single antenna that extends from the chip 36 of the information carrier reader 34 to cover both positions that the information carrier 28 with its antenna 30 may assume, as seen in FIG. 6.

However, it might be necessary to reduce the risk that the antenna 38 interferes with itself because of the semi-circular extension, there might be two antennas 38a and 38b, FIG. 7 positioned opposite each other adjacent either of the positions that the information carrier 28 and its antenna 30 may assume. Further, the chip 36 of the information carrier reader 34 may be programmed such that the reading procedure is cycled between the two antennas 38a and 38b, so that only one antenna is read at the time.

Even though the embodiment has shown that the proximal part may be attached in two positions and that the antenna arrangement 38 can handle both positions, it is to be understood that the attachment arrangement may comprise more than two positions that the information carrier may assume, for instance four, and then the antenna arrangement is modified in corresponding way with either one antenna that covers all four positions or four antennas that cover each position. It may also be that it is sufficient with two antennas, where each antenna may cover two adjacent positions that the information carrier may assume.

Further, the attachment arrangement may have different shapes and functions. For instance there might be a bayonet-type attachment for attaching and locking the proximal part to the distal part. Also threaded attachment arrangements are feasible, wherein the information carrier may assume different positions depending on start engagement of the threads when attaching the medicament delivery device parts to each other.

It is to be understood that the embodiment described above and shown in the drawings is to be regarded only as non-limiting examples of the application and that it may be modified in many ways within the scope of the patent claims.

The invention claimed is:

1. A medicament delivery device comprising:
   a proximal part and a distal part;
   a medicament container positioned within and surrounded by the proximal part;
   an information carrier reader affixed to the distal part, where the information carrier reader is located at a proximal end of the distal part and comprises a distal antenna;
   an information carrier affixed to the proximal part and not the medicament container, where the information carrier is located at a distal end of the proximal part in alignment with the information carrier reader and comprises a proximal antenna; and
   an attachment arrangement for attaching the proximal part to the distal part, which attachment arrangement is designed such that the information carrier can be in two different positions when the proximal part is attached to the distal part,
   wherein alignment of the information carrier reader with the information carrier allows the distal antenna to operatively connect to the proximal antenna such that the information carrier reader reads information from the information carrier in either one of the two different positions that the information carrier may assume.

2. The medicament delivery device according to claim 1, wherein the distal antenna comprises two antennas positioned on a flexible holder that is shaped to cover a circumferential portion of the proximal end of the distal part such that the proximal antenna will axially aligned with one of the two distal antennas when the information carrier is in either of the two different positions when the proximal part is attached to the distal part.

3. The medicament delivery device according to claim 1, wherein the proximal part further comprises a distally directed tongue that fits into a recess inside a tubular passage of the distal part to form a lock when the distal part and proximal part are attached.

4. The medicament delivery device according to claim 2, wherein a distal end of the proximal part forms a first engagement area that is designed to fit into and engage with a second engagement area of a cavity of said distal part such that the distal part and the proximal part can rotate relative to each other to axially align the proximal antenna with one of the two distal antennas.

5. The medicament delivery device according to claim 4, wherein the antenna of said information carrier is arranged in the first engagement area of the proximal part.

6. The medicament delivery device according to claim 5, wherein said at least one antenna of the information carrier reader is arranged and extending in said second engagement area so as to enable reading of said information carrier in any of the rotational position that the information carrier assumes.

7. The medicament delivery device according to claim 6, wherein said first and said second engagement areas have cylindrical shapes, wherein said at least one antenna of the information carrier reader is extending around a substantial part of the circumference of the second engagement area.

8. The medicament delivery device according to claim 1, wherein said at least one antenna of the information carrier reader is a single antenna.

9. The medicament delivery device according to claim 1, wherein said at least one antenna of the information carrier reader comprises several antennas.

10. The medicament delivery device according to claim 9, wherein different antennas are arranged to cover different positions that the information carrier assumes.

11. The medicament delivery device according to claim 10, wherein the information carrier reader is programmed such that only one antenna is active at the time so as not to interfere in the reading of the information carrier.

12. The medicament delivery device according to claim 1, wherein the proximal part is disposable after use.

13. The medicament delivery device according to claim 1, wherein the proximal part is reusable and the medicament container is disposed after use.

14. A medicament delivery device comprising:
   a proximal part comprising an information carrier having a first antenna; and
   a distal part comprising an information carrier reader having a second antenna positioned on a flexible holder that is shaped to cover a circumferential portion of the proximal end of the distal part such that the first antenna will axially aligned with the second antenna when the information carrier is in either of two different positions when the proximal part is attached to the distal part, wherein a distal end of the proximal part has a first engagement area configured to attach to a second engagement area located at a proximal end of the distal part, where physical engagement of the first engagement area with the second engagement area allows the proximal part to lock to the distal part in a first position and to lock in a second position, wherein the second antenna is arranged such that it is capable of reading information from the information carrier in either the first position or the second position, and wherein the first antenna is arranged in the second engagement area and the second antenna is arranged in the first engagement area.

15. The medicament delivery device of claim 14, wherein the second position is oriented 180 degrees relative to the first position.

16. The medicament delivery device of claim 14 wherein the first and said second engagement areas are cylindrical shaped and the first antenna circumferentially extends around a part of the second engagement area.

17. The medicament delivery device of claim 14 wherein the lock is formed by engagement of tongue comprising a protrusion with an inner surface of the first engagement area.

18. The medicament delivery device of claim 14, wherein the information carrier further comprises additional antennas.

19. The medicament delivery device of claim 18, wherein the information carrier reader is programmed such that only one of the second antenna and the additional antennas is active at one point in time so as not to interfere in the reading of the information carrier.

20. The medicament delivery device of claim 1, wherein data obtained by the information carrier reader is transmitted to an external source for data handling.

* * * * *